United States Patent [19]

Wadsworth

[11] 4,198,389

[45] Apr. 15, 1980

[54] DETERMINATION OF IMMUNOLOGICALLY ACTIVE MATERIALS AND SYSTEM THEREFORE

[75] Inventor: Charles Wadsworth, Göteborg, Sweden

[73] Assignee: Hoffmann-La Roche Inc., Nutley, N.J.

[21] Appl. No.: 825,500

[22] Filed: Aug. 17, 1977

[30] Foreign Application Priority Data

Aug. 20, 1976 [SE] Sweden .................................. 7609263

[51] Int. Cl.² ...................... G01N 21/00; G01N 27/00; G01N 31/02; G01N 33/16
[52] U.S. Cl. ...................................... 424/8; 23/230 B; 204/180 G; 204/299 R; 422/56; 424/3; 424/11; 424/12; 424/13
[58] Field of Search ..................... 424/3, 8, 11, 12, 13; 23/230 R, 230 B; 204/299 R, 180 G; 422/56

[56] References Cited

U.S. PATENT DOCUMENTS

| | | | |
|---|---|---|---|
| 4,020,151 | 4/1977 | Bolz | 424/8 X |
| 4,025,310 | 5/1977 | Bolz | 424/12 X |

OTHER PUBLICATIONS

Wilson, J. of Immunology, vol. 92, 1964, pp. 431–434.
Alper, Voxsang., vol. 17, 1969, pp. 445–452.
Grabar, Biochim. et Biophys. Acta, vol. 17, 1955, pp. 67–74.
Feinberg, Nature, vol. 194, Apr. 21, 1962, pp. 307–308.

*Primary Examiner*—Anna P. Fagelson
*Attorney, Agent, or Firm*—Jon S. Saxe; George M. Gould; James H. Callwood

[57] ABSTRACT

A method and system for a rapid and sensitive method for determining immunologically active materials in a biological fluid by observing an antigen-antibody reaction after application of reactants on the surface of a gel matrix and applying an alternating current thereto.

19 Claims, 2 Drawing Figures

DETERMINATION OF IMMUNOLOGICALLY ACTIVE MATERIALS AND SYSTEM THEREFORE

BACKGROUND OF THE INVENTION

Diagnostic methods based on an antigen-antibody reaction in a gel are well-known in the art. In recent years the methods employing radial immunodiffusion like that described by Mancini et al. (Protides Biol. Fluids 11, 370, 1964) and methods utilizing the electroimmunoassay of Laurell (Anal. Biochem. 15, 45, 1966) have become so widespread that ready to use plates and standards are commercially available for measuring human serum proteins, particularly the immunoglobulins A, G and M. Unfortunately these methods have the disadvantage of giving large errors in quantitation which have been demonstrated when the tested samples and standards diverge in character, for example, in regard to molecular size.

With the Mancini's method differences in diffusibility are held culpable while for Laurell's method, among other things variations in electromobility and diffusibility are considered responsible for quantitating discrepancies.

Additional prior art in this area includes U.S. Pat. No. 3,853,468 which utilizes a substrate coated with a substance, i.e., acrylic or other plastic, which has affinity for nonagglutinated particles as a means of determining the presence or absence of antibodies or antigens in sample biological fluids. The patent also describes use of an absorbent material to remove non-absorbed material. Furthermore, U.S. Pat. No. 3,905,767 detects the antibody-antigen reaction by incorporating one component as part of a gel and adding the other component to the surface to form a precipitate on the surface. Light scattering is utilized to detect the presence of the precipitate.

DESCRIPTION OF THE INVENTION

The present invention which is based on the fact that antigens as well as their specific antibodies are soluble in an aqueous solution while the products of their immuno-precipitation are insoluble avoids the influence of diffusion and electromobility. In fact the present invention overcomes the disadvantages of the previous methods and provides a novel method which is rapid, accurate, simple to perform and cheap.

More particularly the present invention relates to a process for determining an immunologically active material in a fluid, comprising using an inert gel matrix on a non-reactive support, applying an aliquot of a sample of the fluid onto the gel, covering the area of application with a solution containing a specific counter-reactive material, removing the unreacted soluble materials and observing the results of the immunological reaction.

Furthermore the present invention relates to a process for determining the content of total protein in a fluid, comprising using an inert gel matrix on a non reactive support, applying an aliquot of a sample of the fluid onto the gel, chemically fixing the proteins and observing the results of the reaction.

The term "immunologically active material" refers to components of physiological fluids, cell and tissue extracts for which an immunological counterreactant is available or can be produced. Typical immunological materials are primary amines, aminoacids, peptides, proteins, lipoproteins, glycoproteins, sterines, steroides, lipoides, nucleic acids, enzymes, hormones, vitamines, polysaccharides and alcaloides.

Examples of such immunologically active substances are given in the following table:

TABLE I

I. Microorganisms

Bacteria
1. Gram-positive cocci
   Streptococci (*pyogenes, fecalis* and *viridans*)
   Staphylococci (*aureus* and *albus*)
   Pneumococci (*D. pneumoniae*)
2. Gram-negative cocci
   Neisseria (*gonorrhoeae* and *meningitidis*)
3. Gram-positive aerobic bacilli
   *Bacillus anthracis*
   *Corynebacterium diphtheriae*
   Erysipelothrix
   *Listeria monocytogenes*
4. Gram-positive anaerobic bacilli
   Clostridia (*botulinum, perfringens, welchii* and *tetani*)
5. Gram-negative anaerobic bacilli
   Bacteroides
6. Gram-negative intestinal bacilli
   Escherichia
   Klebsiella
   Enterobacter
   Proteus
   Pseudomonas
   Salmonella
   Shigella
7. Gram-negative nonintestinal bacilli
   Pasteurella (*pestis* and *tularensis*)
   *Hemophilus influenzae*
   Brucella (*melitensis, abortus* and *suis*)
   *Bordetella pertussis*
   Malleomyces
8. Spirochetes
   *Treponema pallidum*
   Leptospira
   Borrelia
9. Mycoplasma
10. Mycobacteria
11. Vibrio
12. Actinomyces Protozoa
1. Intestinal Protozoa
   Amebae
2. Flagellates
   Trichomonas
   Leishmania
   Trypanosomes
   Toxoplasma
3. Sporozoa
   Plasmodia (*vivax, falciparum, malariae* and *ovale*)
4. Intestinal nematodes
   Pinworms
   Hookworms
   Whip worms
5. Tissue nematodes
   Trichinella
   *Filaria (Wuchereria bancroftii)*
   Dracunculus
6. Trematodes
   Schistosomes
   Intestinal flukes Tissue flukes
7. Cestodes
   Tapeworms
8. Toxoplasma (*T. gondii*)

Fungi
1. Sporotrichum
2. Cryptococcus
3. Blastomyces
4. Histoplasma
5. Coccidioides
6. Candida Viruses and Rickettsia
1. Rickettsia
2. Viruses
   Canine hepatitis
   Shope papilloma
   Influenza A & B
   Fowl plague
   Herpes simplex
   Adenoviruses
   Polyoma
   Rous sarcoma
   Vaccinia
   Poliovirus
   Measles
   Canine distemper
   Leukemia
   Mumps
   Newcastle disease
   Sendai
   ECHO
   Foot and mouth disease
   Psittacosis
   Rabies
   Extromelia
   Arbor viruses II. Tissue antigens including organ specific antigens Polysaccharides
Hyaluronidase
Tetanus toxin
Egg ovalbumin
Ovine serum albumin
Kidney
Liver
Skin
Heart
Gastrointestinal tract
Prostate
Embryonic antigens (alpha 1 fetoprotein)
Tumor antigens (carcinoembryonic antigen)
Muscle
Collagen
Amyloid III. Hormones Pituitary hormones
Insulin
Glucagon
Thyroid hormone
Chorionic gonatropin
Chorionic growth hormone—prolactin IV. Enzymes Pancreatic chymotrypsinogen
Procarboxypeptidase
Deoxyribonuclease
Ribonuclease
Glyceraldehyde-3-phosphate dehydrogenase
Catalase
Peroxidase V. Blood Cell Antigens, Blood Group Substances and other Isoantigens Platelets
Megakaryocytes
Leucocytes
Erythrocytes
Blood group substances
Forssman antigen
Histocompability antigens VI. Plasma Proteins Fibrin and fibrinogen
Plasminogen and plasmin
Albumin
Immunoglobulins
$\alpha$-1-antichymotrypsin
$\alpha$-1-antitrypsin
Complement factors
Ceruloplasmin
Gc-globulin
Haptoglobin
$\alpha$-2-macroglobulin
$\beta$-2-microglobulin
Orosomucoid
Prealbumin
Transferrin VII. Milk Proteins Lactoferrin
Lysozyme
Secretory IgA
Secretory IgM
Secretory component VIII. Saliva Proteins Secretory IgA
Secretory IgM
Secretory component IX. Uring Proteins X. Pathologic Proteins Myeloma protein
Macroglobulinaemic proteins
Dysglobulinaemic proteins
Bence Jones I, II proteins
C-reactive protein
Cryoglobulins XI. Antibodies including autoantibodies Antinuclear factor
Thyroid autoantibodies
Anti-Tamm-Horsfall protein
Cold agglutinins
Rheumatoid factor
Adrenal autoantibodies
Autoantibody to gastric parietal cells in pernicious anemia
Anti-colon
Anti-liver
Anti-kidney
Autoantibodies to spermatozoa
Anti-heart
Muscle autoantibodies in myasthenia gravis Autoantibodies to nervous tissue
Autoantibodies against fibrous tissue and vascular components
Autoantibodies against platelets and megakaryocytes
Antibodies against trophoblasts
Antibodies to microorganisms
Antibodies to animal antigens
Antibodies to drugs Particularly preferred immunologically active materials are IgA, IgG, IgM, CRP (C-reactive protein) in serum and the secretory IgA and IgM in milk.

The gel used according to the present invention can be selected from one of the many gel-forming immunologically inert materials like agar, agarose, cellulose acetate, starch gel, gelatin, polyacrylamide or combinations thereof.

The gel may contain in addition an electrolyte and/or a surface tension decreasing detergent.

In the context of this invention the term "fluid" encompasses biological fluids for example serum, plasma, milk, urine, saliva or spinal fluid, amniotic fluid, synovial fluid, extravascular fluid and other secretions and excretions from humans and animals as well as aqueous extracts from any living source.

All types of non reactive support are suitable in accordance with the present invention, for example plates, slides or films which are used in the medical field or in laboratories. The support can consist of any suitable material such as, for example, glass or synthetic material and is preferably transparent.

The term "aliquot of a sample" or "drop" as used in the context of this invention means microliter amounts up to about 10 $\mu$l usually 1-4 $\mu$l of the fluid to be investigated. These microliter amounts of the fluid to be tested are preferably applied by means of microapplicator such as a micropipette.

The solution of counterreactive material which is applied to cover the area of application of the aliquot of sample of the fluid to be analyzed contains any substance able to react immunologically with the material to be determined.

Although other immunological systems e.g. based on a double antibody method or competitive reaction using labelled or conjugated reactants can be envisaged, the most preferred embodiment of the present invention is to use a solution of counterreactive material containing for the determination of an antigen an antibody specific for said antigen and for the determination of an antibody the corresponding antigen.

While the amount of the solution containing the counterreactive material is not really critical, it is crucial that it exceed the first applied aliquot in volume so that all of the immunologically active materials in the sample have an opportunity to react with their counterparts.

The solution containing the immunological counterreactive material is preferably an aqueous solution which may contain additives usually employed in immunological tests, e.g. phosphate buffered saline.

In the process of the invention the pH should be preferably maintained between 5 to 9 in order to avoid a denaturation of the immunologically active materials involved in the reaction. This can be achieved with appropriate conventional buffer systems such as phosphate or barbital buffers.

The observation of the results of the immunological reactions depends on the nature of the test and the mode of visualization to be employed. Visualization methods which can be used in the context of this invention are for example, radiodetection, fluorometric detection, enzymatic detection, spectrophotometric detection, visual inspection.

In a preferred embodiment of the invention the results are observed spectrophotometrically or visually after staining.

According to one preferred embodiment of the invention, a drop of fluid subjected to investigation, containing the antigen, possibly diluted and/or treated e.g. by heating so that the component of interest is demonstrable, is added on a gel matrix. The drop is covered with an excess of antibody, the non-reactive antigens and the excess of antibodies are washed away, the products of the immuno-precipitation are stained and the result compared with a known color scale. If the amount of a certain antibody in a serum is to be determined the order of application is reversed and first a drop of serum and afterwards a drop of antigen are applied. The gel matrix preferably placed on a glass plate or the like and a number of parallel tests are made in order to obtain safe values.

It is also possible to determine the amount of different antigens or antibodies simultaneously. For this purpose drops of the fluid to be analysed (primary fluid) are spread in a pattern over the gel matrix and the drops in the individual sections covered with various counter-reactive fluids (secondary fluids) containing different sorts of antibodies or antigens reacting specifically with the antigens or the antibodies in the primary fluid.

In certain cases it may be interesting to determine the total amount of protein in a certain fluid in addition to the amount of a certain or of certain specific antigens. For this purpose one can according to one further embodiment of the invention, chemically fix all proteins in some of the drops and, treat the other drops with antibodies so that on the same matrix one obtains on the one hand the value of total protein and on the other hand one or more partial values.

In order to achieve an even penetration of the drops into the gel matrix it is convenient for the latter to contain a certain amount of a surface tension decreasing solution. The uptake takes place relatively slowly, and one can expect some spreading.

In order to secure the even distribution of drops it has proved advantageous, at least during the initial phase of the reaction time, to allow an alternating current to pass through the gel matrix. The different molecules in the drop are thus kept together. Voltage between 1 and 3 V per 1 cm matrix between the filter paper bridges at the edges of the plate gives satisfactory results, a voltage of 2.5 V being preferred.

In certain cases the antigen may be bound to another molecule, e.g. albumin. When the antigen binds with its antibody and becomes insoluble, the other molecule remains. One may be interested to determine the amount of antigen plus the other molecule, e.g. the albumin. In one specific embodiment one proceeds as described above, i.e. one applies on the matrix a pair of drops of the primary fluid containing the antigen-albumin complex, applies a suitable amount of the secondary fluid containing the antibody specific to the antigen on the drops of primary fluid and allow the components to react, thereafter the soluble components are removed by washing. The albumin bound to the antigen remains.

Then one applies a certain amount of a fluid containing an antibody specific for albumin on the reacted material of one of the drops and after a suitable reaction time the unreacted material not specific for albumin is washed away. Thereafter the final products of the immunoprecipitation are stained.

For the purpose of quantification one can use an earlier prepared color scale, but it is more suitable to produce at least three standards containing different known quantities of the investigated component, directly on the matrix. In this way one avoids any error in nuances due to differences in performing the test.

The invention is further illustrated by the following description, with reference to the drawings.

In the drawings.

Figure 1:
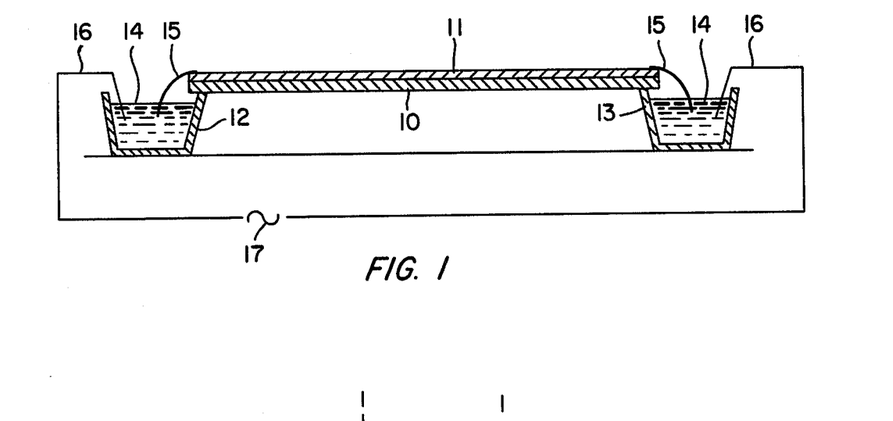
FIG. 1 schematically represents one specific embodiment of a device suitable for performing the method of the invention.

In FIG. 1 the number 10 represents a glass plate or a plate of a transparent nonreactive material. On this plate a gel matrix 11 is placed containing agar or agarose and a minor quantity of a solvent decreasing the surface tension. In this particular case the gel also contains an electrolyte.

The plate 10 is lying horizontally on two reservoirs 12 and 13 containing a fluid 14, usually the same as the electrolyte in the gel. The gel matrix 11 is connected with the fluid 14 in reservoirs 12 and 13 by means of bridges 15 of filter paper, or the like. Contacts 16, connected to an alternating current supply 17, are also dipped into the fluid 14.

In operation small drops of the primary biological fluid to be investigated are applied on the gel matrix, and each of the drops is covered with a larger volume of a secondary fluid containing the counterreactant to the investigated component, i.e. monospecific antibodies when the task is to determine a certain antigen, or a suitable antigen when the task is to determine the amount of a certain antibody in serum or another body fluid.

Figure 2:
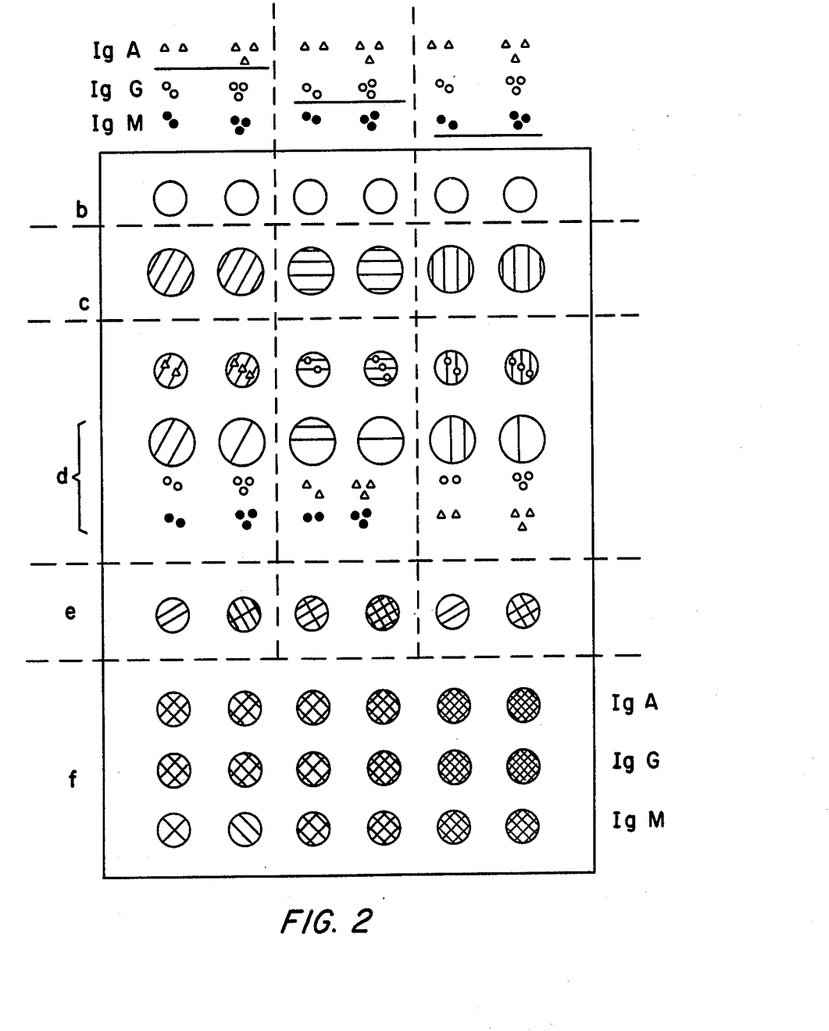
FIG. 2 schematically shows the more important stages in a specific embodiment of a procedure for determining simultaneously three different components (IgA, IgG and IgM).

The essential procedure is more evident from FIG. 2 showing a matrix with applied fluid drops and reaction products.

The fluid to be investigated is assumed to contain antigens IgA, IgG and IgM (plus possibly other soluble components). The antigens in question are at the top of the matrix marked with various symbols to be distinguishable.

The matrix is symbolically divided into three vertical fields, and in each of these one applies two drops of the primary fluid for the purpose of illustration the drop to the right in each field is assumed to refer to a set with a content of antigens higher than the drop to the left.

The matrix is moreover symbolically divided horisontally, and in the left margin a letter is found referring to a certain stage of the procedure.

The uppermost, horizontal band marked (b) represents the application of small drops of the primary fluid. The subsequent band marked (c) represents the application of larger drops of the secondary fluids.

It is further assumed that in the left—vertical—field one intends to determine the amount of IgA, in the middle portion the amount of IgG and in the right portion the amount of IgM. Thus in this case one uses three different secondary fluids, each of which contains monospecific antibodies to IgA, IgG or IgM.

In the subsequent horizontal band the insoluble products of the immunoprecipitation are shown. A portion (bracket d) of this band shows the soluble excess antibodies and the soluble unreacted antigens in each vertical field. These soluble components are washed away at least once with a buffer solution. Thereafter an absorption paper is pressed against the matrix so that soluble components which have not taken part in the reaction and remain soluble are removed.

Thereafter the reaction components are stained and the gel matrix surrounding these reaction components is destained. Differences in nuances indicating quantities of precipitated reactants are shown in band (e) and should be compared to a color scale. This can be done with a separate scale, prepared in advance, but in order to avoid possible variations which might occur due to the mode of procedure it is advisable to establish each time a standard color scale, directly on the matrix, as shown by band (f).

In this case one uses solutions with known quantities of the relevant antigens and applies them in rows on the matrix. One either has a stock solution with high concentration and dilutes it or one has many different solutions with known, stepwise varying, concentrations. In the present case there are six different color grades, and the concentration increases in the direction from left to right.

The procedure follows the same pattern as described above, i.e. ones applies the necessary number of drops of the primary fluid, thereafter the corresponding number of drops of the secondary fluids, washes dries and stains concurrently with the processing in the corresponding vertical field. The scales for IgA and IgG are approximately identical while the one for IgM is somewhat weaker than the other two.

The following examples further illustrate the invention.

EXAMPLE 1

Determination of the amount of an arbitrary protein-antigen. One selects a gel, e.g. containing 1% agarose and 0.01% Tween 80 and spread to a 1 mm thick layer on a glass plate. The gel also contains an electrically conductive component e.g. 37.5 mmol veronal per 1 liter with a pH of 8,6. The gel layer is connected by bridges of filter paper with vessels containing a veronal buffer at 75 mmol per 1 liter. The vessels are fitted out to be connected to an alternating current supply with a voltage of 2.5 v per 1 cm across the matrix.

The current is on while appling the primary fluid and for 15 minutes after application of the secondary fluid. Thereupon the plate is left without current about 10 minutes.

The proteins that have not reacted are still soluble, and the plate with the gel matrix is submerged a couple of times into a phosphate buffered saline and pressed, after each dipping, under a about 1 kg weight, with a thick absorption paper that takes up the insoluble proteins and salt solutions. The treatment is repeated until one is sure that all soluble components have been removed.

The staining is in this case done with a "Coomassie Blue R" solution.

Afterwards one decolors the gel matrix to obtain a clear background to contrast with the immunoprecipitate.

As already pointed out, one can use separate standard color scales or prepare such directly on the matrix.

EXAMPLE 2

Simultaneous quantitation of several antigens, e.g. IgA, IgG and IgM (FIG. 2).

One makes several applications in a regular pattern and covers the areas within the individual sections of the pattern with antisera corresponding to the different antigens, and thereafter one washes, presses, dries, stains and observes the obtained color grades as in the example 1.

EXAMPLE 3

Determination of the amount of complexed antigens, e.g. IgG-albumin, IgG-IgA or IgG-IgM in human serum.

One proceeds in the same way as described above in the Example 1, i.e. one adds one or more drops of the fluid to be investigated on the matrix and covers them first with the solution containing antibodies specific for one component in the complex and then washes the matrix. Thereafter one covers the areas of application with another solution containing antibodies specific for the other component in the complex and finally proceeds according to the steps in the previous examples.

In case one wishes to determine in addition to the total amount of the complexed antigens, the quantity of one of the components in said complex one applies two drops or two rows of drops and treats the one drop or the one row of drops according to Example 1 for quantitation of an individual component, and the other drop or row of drops according to the description in the previous paragraph. A suitable color scale or portions representing the components individually or as complexed antigens should be included on the matrix.

EXAMPLE 4

Characterization and quantitation of human IgA.

A solution of gel is prepared by dissolving (boiling) 0.5 g of agarose (Bio-Rad) in 25 ml of distilled $H_2O$ and kept at 55°-60° C. 10 ml of this solution are mixed with 10 ml of buffer, i.e. barbital-barbital Na (Merck) 75 mmol/l, $NaN_3$ 6 mmol/l, pH 8.6 with an addition of Tween 20 to 0.01% also at 55°-60° C. The mix is poured on a level, glass plate (12×16×0.1 cm) and allowed to gelify in an $H_2O$-saturated milieu providing a gel matrix with a thickness of about 1 mm.

Antigen solutions are prepared from a pool of blood donor sera (HS St) which have been rated for concentration of immunoglobulin A, G and M with the World Health Organization reference standard 67/97. The diluent is PBS (phosphate buffered saline), pH 7.1. The immunoglobulin fraction of rabbit anti-human IgA specific for α-chains (Dakopatts, Brostex A/S, Copenhagen) is diluted with PBS to a strength of 133 μg per ml, i.e. 1 ml antiserum can bind 133 μg of specific antigen (manufacturer's description).

The plate (glass support and gel matrix) is placed horizontally on a suitable electrophoresis apparatus with two vessels containing the aforementioned barbital buffer without the Tween. Filter paper (Whatman no. 3) bridges are placed to cover about 0.5 cm of the long edges of the gel matrix and to dip into the buffer in the vessels which are fitted with electrodes connected to a veriac transformer fed by a current of 220 V, 50 Hz.

The current is turned on and a potential of 2.5 V/cm across the plate is established. Within 10 min. the application of 4 μl samples of the antigen is started. As soon as the samples are taken up by the gel (about 5 min) the antiserum drops (10 μl) are superimposed. The reactants are applied within 15 min. The apparatus is covered to protect the plate against evaporation and dust. Forty min. after the last antigen drop is covered with antiserum the current is disconnected and the plate allowed to stabilize for 10 min.

The plate is removed from the apparatus, rinsed with PBS, and covered with filter paper, a 0.5–1.0 cm thick layer of absorbent paper, a glass plate and a weight of 1–2 Kg. About 15 min later when the liquid and soluble components in the agarose have been eluted by the absorbent paper, this and the filter paper are removed. The agarose film is swollen for 5 min. with fresh PBS under a new filter paper piece. Ten min. later it is pressed again with a fresh filter paper, absorbent paper, the glass and the weight. The pressing is repeated a third time, but thereafter the filter paper is left in place and the agarose film permitted to dry.

The antigen-antibody precipitates in the dry agarose film are stained for 10 min. in a Coomassie Brilliant Blue R (Sigma) stain bath: 2.5 g dye per liter of glacial acetic acid, ethanol 95%, distilled $H_2O$ (1+3.5+5.5 parts, respectively). After a rinse with running tap water, destaining is performed in a bath of the aforementioned solvents (1+2.5+6.5 parts, respectively) until the background to the stained spots is clear.

The precipitate color intensity is registered with a Chromatogram Spektralphotometer KM3 (Carl Zeiss, Oberkocken, West Germany). The plate is passed through a light beam of 0.1 mm×10 mm at a rate of 30 mm/min. Absorbance at 558 nm is monitored as a curve with an Hitachi Perkin-Elmer recorder 165 at 5 mV and a chart speed of 60 mm/min. The area of the scribed peaks representing amount of precipitate is calculated as height times the width at ½ the height of the peak.

The concentration of IgA in the dilutions of HS St and the areas in $mm^2$ divided by 40 of the recorded curve peaks are given in Table 1.

Table 1

| IgA concentration g/l | Peak area $mm^2$/40 |
| --- | --- |
| 0.0085 | 4.4 |
| 0.0085 | 4.9 |
| 0.0143 | 8.8 |
| 0.0215 | 14.7 |
| 0.0285 | 17.5 |
| 0.0285 | 17.6 |
| 0.0343 | 20.3 |
| 0.0428 | 22.4 |
| 0.0428 | 22.4 |
| 0.0573 | 30.5 |

The calculated areas of the peaks show that as the concentration of antigen increases so does the area of the scribed peak, i.e. more precipitate is formed which leads to more dye being taken up and registered as a proportional increase in area of the scribed peaks. Thus the amount of stain depends on the concentration of antigen and this parameter may be used for quantitating IgA.

EXAMPLE 5

Characterization and quantitation of human IgG.

The plate is prepared and the procedure carried out as described in Example 4 except that the immunoglobulin fraction of rabbit antiserum to human IgG (γ-chain specific, Dakopatts) is substituted for anti-IgA. It is diluted to a concentration of 200 µg per ml. The results are given in Table 2.

Table 2

| IgG concentration g/l | Peak area mm²/40 |
|---|---|
| 0.0100 | 5.9 |
| 0.0168 | 10.2 |
| 0.0250 | 14.4 |
| 0.0333 | 22.9 |
| 0.0400 | 24.6 |
| 0.0500 | 29.4 |

It may be observed that the areas of the scribed peaks are proportional to the antigen concentrations indicating that the process may be used for quantitating IgG.

EXAMPLE 6

Characterization and quantitation of human IgM.

The plate was prepared and the procedure carried out as described in Example 4 with the exception that the immunoglobulin fraction of rabbit antiserum to human IgM (µ-chain specific, Dakopatts) is used instead of anti-IgA. It is diluted to 200 µg/ml. The observed results are given in Table 3.

Table 3

| IgM concentration g/l | Peak area mm²/40 |
|---|---|
| 0.0158 | 3.0 |
| 0.0263 | 6.0 |
| 0.0395 | 9.1 |
| 0.0528 | 11.6 |
| 0.0633 | 14.2 |
| 0.0790 | 17.2 |

It is seen that the areas of the scribed peaks are proportional to the antigen concentrations, therefore the process may be used for quantitating IgM.

EXAMPLE 7

Quantitation of human IgG in the presence and absence of an alternating current potential, during different periods of time.

Two plates are prepared as described in Examples 4 and 5 except that one plate is supported horizontally with no connection to a source of alternating current. The procedure with both plates is carried out as in Example 4 except that the antigen and antiserum solutions, IgG and anti-IgG as in Example 5 are applied at intervals to allow reaction times of 20, 40, 60, or 80 min. The observed results are indicated in Table 4.

Table 4

| IgG concentration g/l | 20 min Volts/cm | | 40 min Volts/cm | | 60 min Volts/cm | | 80 min Volts/cm | |
|---|---|---|---|---|---|---|---|---|
| | 2.5 | None | 2.5 | None | 2.5 | None | 2.5 | None |
| 0.010 | 10.0 | 8.8 | 12.7 | 9.8 | 13.2 | 13.5 | 13.5 | 11.9 |
| 0.024 | 19.5 | 19.2 | 23.2 | 20.9 | 25.8 | 24.6 | 26.3 | 24.5 |
| 0.025 | 25.2 | 26.3 | 27.6 | 23.0 | 27.6 | 24.8 | 30.3 | 26.8 |
| 0.033 | 29.4 | 26.7 | 34.2 | 33.0 | 34.5 | 28.6 | 41.3 | 32.9 |
| 0.045 | 39.1 | 35.5 | 46.5 | 39.2 | 45.6 | 43.2 | 47.6 | 44.5 |
| 0.050 | 42.7 | 40.1 | 48.3 | 41.8 | 48.5 | 45.3 | 48.5 | 46.2 |
| 0.083 | 59.1 | 56.6 | 74.4 | 62.3 | 67.3 | 67.9 | 72.5 | 68.8 |

The peak areas representing precipitated IgG at all concentrations of antigen increase in relation to longer reaction time. Except in 3 instances, the areas measured in the presence of alternating current (AC) are higher than those registered in its absence. With the current, the amount of precipitate increases on the average by 18.6% between 20 and 40 min., hardly changes during 40 to 60 min. and rises 6.6% from 60 to 80 min. of reaction time. Without current the average percentual increases in precipitate for these time periods are: 8.0%, 8.0% and 2,4%, respectively. Thus IgG applied within 20 min. and reacting with anti-IgG for 40 to 60 min would be more suitably quantitated with an alternating current milieu than without it.

EXAMPLE 8

Characterization and quantitation of human immunoglobulins A, G and M and the photometric results analyzed with an alternative method.

A plate is prepared and the procedure carried out according to Examples 4, 5 and 6, i.e. dilutions of human serum are quantitated for immunoglobulins A, G or M. Three microliters of antigen and 6 microliters of antiserum are used. After photometric registration of the degree of staining the height in mm of the scribed peaks is related to the concentration of the analyzed immunoglobulin, see Table 5A, B and C.

Table 5

| Immunoglobulin and concentration, g/l | Peak height, mm |
|---|---|
| A. IgA | |
| 0.0085 | 14.0 |
| 0.0085 | 17.0 |
| 0.0143 | 29.0 |
| 0.0215 | 46.0 |
| 0.0285 | 57.5 |
| 0.0285 | 56.0 |
| 0.0343 | 66.5 |
| 0.0428 | 74.5 |
| 0.0428 | 70.0 |
| 0.0573 | 100.0 |
| B. IgG | |
| 0.0100 | 21.5 |
| 0.0168 | 35.5 |
| 0.0250 | 50.0 |
| 0.0333 | 72.5 |
| 0.0400 | 82.0 |
| 0.0500 | 99.0 |
| C. IgM | |
| 0.0158 | 3.0 |
| 0.0263 | 6.0 |
| 0.0395 | 9.1 |
| 0.0528 | 11.6 |
| 0.0633 | 14.2 |
| 0.0790 | 17.2 |

The scribed peaks are proportionally higher in relation to increasing immunoglobin concentration. Thus, the peak height in mm representing the intensity of stained precipitate can be employed as a measure of the amount of analyzed antigen in the stained spot.

EXAMPLE 9

Characterization and quantitation of human immunoglobulins A, G and M, the results being observed by visual inspection.

A plate is prepared and the procedure carried out as in Example 8 except that the results are observed by visual inspection as well as photometric registration. Standard reference spots representing known amounts of antigen for each class of immunoglobulin are included on the plate. The measured peak heights in mm are plotted against the known µg of antigen for IgA, IgG of IgM. From these curves the amount of IgA, IgG or IgM in the test spots is determined and converted, using the dilution factor and volume of applied sample, to establish the concentration of immunoglobulin in the tested serum.

The visual inspection mode of quantitation is carried out with the plate, gel side down, on a white, matt ground. The intensity of color in a test spot is compared with the different grades of color noted for the corresponding standard reference spots and the amount of antigen forming the test spot estimated.

The concentration of immunoglobulin in the tested serum is calculated, as before, using the dilution factor and sample size. Results observed with these modes of estimation comprise Table 6A, B and C.

Table 6

| Amount, μg, of immunoglobulin in spot | | Concentration of immunoglobulin g/l, in the tested serum | |
|---|---|---|---|
| Photometry, height curve | Visual inspection | Photometry, height curve | visual inspection |
| A. IgA | | | |
| 0.204 | 0.230 | 2.14 | 2.42 |
| 0.182 | 0.200 | 1.91 | 2.10 |
| 0.132 | 0.139 | 1.39 | 1.46 |
| 0.126 | 0.139 | 1.32 | 1.46 |
| 0.113 | 0.116 | 1.18 | 1.22 |
| 0.059 | 0.050 | 0.62 | 0.53 |
| B. IgG | | | |
| 0.238 | 0.225 | 24.99 | 23.63 |
| 0.203 | 0.205 | 10.63 | 10.66 |
| 0.198 | 0.193 | 10.40 | 10.04 |
| 0.174 | 0.193 | 9.14 | 10.04 |
| 0.072 | 0.070 | 7.46 | 7.35 |
| 0.069 | 0.064 | 7.25 | 6.72 |
| 0.062 | 0.050 | 6.46 | 5.25 |
| 0.032 | 0.030 | 3.36 | 3.15 |
| C. IgM | | | |
| 0.300 | 0.291 | 1.58 | 1.53 |
| 0.219 | 0.245 | 1.15 | 1.29 |
| 0.178 | 0.161 | 0.93 | 0.85 |
| 0.145 | 0.148 | 0.77 | 0.78 |
| 0.027 | 0.035 | 0.14 | 0.18 |

The table shows that the visual estimations of the amount of immunoglobulin in the spots on the plate are close to those read from the corresponding peak height curves obtained photometrically. Furthermore the calculated concentrations of immunoglobulins A, G or M in the tested sera also agree well.

EXAMPLE 10

Characterization and quantitation of human C-reactive protein (CRP).

The plate is prepared in the same manner as in Example 4 except that 8 ml of 2% agarose is mixed with 12 ml of the barbital buffer modified by addition of Ca lactate, 12.3 mmol/l and at pH 8.2. The analyzed reference consists of a pool of sera containing high concentrations of CRP which has been rated for CRP at the Diagnostic Laboratory, Dept of Immunology, City of Göteborg, Sweden. This is diluted with the aforementioned buffer without Tween to provide standards with different concentrations of CRP.

The immunoglobulin fraction of rabbit antiserum to human CRP (Dakopatts) is diluted ⅓ with PBS.

The employed procedure is essentially the same as in Example 4 except that 3 μl aliquots of antigen are applied and 5 μl volumes of antiserum superimposed. An electric potential of 2.0 V/cm is employed across the plate. At photometric registration 2 mV is used.

The results comprise Table 7.

Table 7

| CRP concentration mg/l | Peak area mm²/40 |
|---|---|
| 1.1 | 7.4 |
| 3.3 | 15.0 |
| 6.7 | 27.0 |
| 12.0 | 46.6 |
| 15.0 | 56.0 |
| 20.0 | 66.6 |

The area of the scribed peaks increases in relation to rising concentration of antigen, indicating proportionally increasing amounts of stained precipitate. Therefore this process is applicable to quantitation of human CRP.

EXAMPLE 11

Rapid characterization and quantitation of CRP in sera from patients.

The plate is prepared as described in Example 10, and the reference standards are the same. Patient sera which have been previously rated for CRP are enriched with known amounts of the undiluted CRP standard and diluted (1/5 and 1/15) with the barbital buffer. Similar dilutions are made with HS St, a blood donor pool with a negative CRP rating. Both of the HS St dilutions are tested without as well as with the antiserum reactant, while only the 1/5 dilutions of the patient sera are tested without antiserum.

The procedure is carried out as described in Example 10 except that the results are determined visually and photometrically as in Example 9. The estimates for the test sera are adjusted by comparison with the color grades of the negative control HS St. Tables 8 A and B give the color reaction of the HS St tested with and without antiserum and those of the CRP standard with applied antiserum at some similar concentrations and dilutions, using peak height as criterion.

Table 8

| CRP concentration mg/l | Serum dilution | Peak height, mm | |
|---|---|---|---|
| | | Anti-CRP | No anti-CRP |
| A. HS St. | | | |
| 0.07 | .1/15 | 5.0 | 2.3 |
| 0.20 | 1/5 | 7.4 | 4.3 |
| B. CRP standard | | | |
| 1.1 | 1/54 | 7.8 | — |
| 4.0 | 1/15 | 17.0 | — |
| 10.0 | — | 32.0* | — |
| 20.0 | 1/3 | 59.2 | — |

*Upper normal limit in this experiment.

In Table 8 it can be seen that human serum very low in CRP concentration may register low peak heights at the employed dilutions but these are much lower than that for the upper normal limit for CRP in serum, as well as those for similar dilutions of the CRP standard.

Results of quantitation of CRP in the enriched sera from patients performed by visual inspection are given in Table 9, along with the calculated concentrations for CRP.

Table 9

| CRP concentration, mg/l | |
|---|---|
| Calculated | Visual estimate |
| 16.8 | 16.2 |
| 33.0 | 35.5 |
| 47.0 | 42.0 |
| 50.0 | 49.0 |

Table 9-continued

| CRP concentration, mg/l | |
|---|---|
| Calculated | Visual estimate |
| 51.0 | 51.0 |
| 99.0 | 99.0 |
| 101.0 | 97.5 |
| 107.0 | 105.0 |

The visual estimates closely match the calculated concentrations indicating that this process read visually is suitable for quantitation of CRP.

EXAMPLE 12

Characterization and quantitation of secretory IgA as well as determination of its proportion of total protein in human milk.

Two plates are prepared as described in Example 4, and with one plate the procedure is the same as described in Example 8. The same sort of standard curve, as described in Example 9 for IgA, is employed to establish the concentration of secretory IgA in samples of human milk and purified secretory IgA.

The procedure with the second plate is modified after antigen application. Suitable dilutions (with PBS) of HS St are used to establish a standard curve according to its content of total protein. Suitable dilutions with PBS of the human milk and purified secretory IgA are also applied. Ten minutes are allowed for uptake of antigen into the gel and then the plate is removed from the apparatus. It is placed for 15 min. in a picric acid bath (5 parts saturated picric acid + 1 part glacial acetic acid) to fix chemically the proteins. The plate is bathed with 95% ethanol and a piece of filter paper placed on the gel. Then it is pressed with absorbent paper, etc. and the basic procedure followed.

Results of such parallel assays for secretory IgA and total protein in human milk comprise tables 10A and B. Some reference figures for total protein (Micro-Kjeldahl, Spectrophotometry and Lowry testing and Amino acid analysis) are included for comparison.

Table 10

| Concentration of secretory IgA g/l | Total protein g/l | Ratio IgA/protein | Reference total protein g/l |
|---|---|---|---|
| A. Human nilk | | | micro-Kjeldahl |
| 1.47 | 11.82 | 0.124 | 10.36 |
| 1.20 | 11.20 | 0.107 | 12.55 |
| 1.10 | 10.54 | 0.104 | 10.90 |
| 0.87 | 6.58 | 0.132 | 7.90 |
| 0.75 | 7.83 | 0.096 | 7.95 |
| B. Purified secretory IgA | | | spectrophotometry |
| 10.89 | 10.59 | 1.03 | 12.00 |
| | | | Lowry |
| 7.54 | 8.13 | 0.927 | 6.00 |
| 3.90 | 3.80 | 1.026 | 3.00 |
| 1.10 | 1.30 | 0.850 | not done |
| | | | amino acid analysis |
| 0.350 | 0.440 | 0.795 | 0.449 |

The table shows a good agreement of total protein measurements for human milk and purified secretory IgA with the figures obtained by means of standard techniques. The proportion of secretory IgA to total protein is very close to 1.0 for the purified samples indicating that the basic process of the invention can be applied to the determination of secretory IgA, per se, or as total protein.

EXAMPLE 13

Evaluation of standards as well as antisera for the determination of secretory IgA in human mammary secretions.

The plate is prepared and the procedure is carried out as described in Example 12. The test samples of antigen have high or low concentrations of secretory IgA, i.e. they are human colostrum samples taken near parturition or human milk samples taken later during lactation. The standards are HS St and a pool of human milk (HM). The latter is rated for IgA content in relation to purified secretory IgA. In addition to the antiserum (anti-IgA, Dako) employed in Example 12 is used the immunoglobulin fraction of anti-IgA, alpha-chain specific, produced in rabbits by Hyland labs.

The concentrations of secretory IgA in various samples of human mammary secretion using HS St or HM as standard and the two commercial antisera are given in Table 11A and B.

Table 11

| | Concentration of secretory IgA g/l | | | |
|---|---|---|---|---|
| | HS St as standard | Human milk as standard | | Ratio with human milk |
| Sampling day from partus | Anti-IgA (Dako) | Anti-IgA (Dako) | Anti-IgA (Hyland) | as standard (Dako/Hyland) |
| A. Human colostrum | | | | |
| −1 | 45.65 | 42.00 | 51.60 | 0.79 |
| 0 | 43.36 | 50.24 | 61.12 | 0.82 |
| +1 | 26.48 | 27.43 | 25.01 | 1.10 |
| +2 | 15.15 | 15.04 | 15.97 | 0.94 |
| +1 | 12.22 | 10.80 | 13.20 | 0.82 |
| +1 | 12.00 | 11.98 | 12.95 | 0.93 |
| +2 | 11.90 | 12.75 | 12.26 | 1.04 |
| B. Human milk | | | | |
| +3 | 6.37 | 6.98 | 5.48 | 1.27 |
| +3 | 2.46 | 2.50 | 3.02 | 0.83 |
| +3 | 1.72 | 1.64 | 1.58 | 1.04 |
| +3 | 1.60 | 1.42 | 1.29 | 1.10 |

The table shows the consistency in amount of secretory IgA at varying concentrations in mammary secretions obtained with serum IgA (HS St) or secretory IgA (HM) as standard. The concentrations found with anti-IgA from different firms when compared give ratios fairly close to 1.0. Thus this process is suitable for analysing the efficacy of different standards and antisera for quantitation of human secretory IgA in mammary secretions.

EXAMPLE 14

Characterization of antisera in regard to the content of antibodies specific for different antigenic determinants on the secretory component (SC) found in human mammary secretions.

The plate is prepared and the procedure is carried out as in Example 13. The test samples of antigen are colostrum and human milk and the standard is HM. The secretory component is found in human secretions in a free form and bound to the dimeric IgA molecule and the complex is known as secretory IgA. Since colostrum has a high concentration of secretory IgA as compared to milk it also has a high proportion of bound SC which carries an antigenic determinant not found on free SC. Immunoglobulin fractions of two different antisera are employed. One (anti-SC bound) was produced (Dakopatts) against SC in normal colostrum the other (anti-SC free) was produced against colostrum from a woman who was deficient in serum and secretory IgA.

The results of analysis of the same dilutions of colostrum and human milk for SC with "anti-SC bound" and "anti-SC free" comprise Table 12. The concentrations of secretory IgA in the samples are given for reference purposes.

Table 12

| | Concentration of secretory IgA g/l | | |
|---|---|---|---|
| Sampling day from partus | Anti-IgA diluted (1+2) | Anti-SC free diluted (1+2) | Anti-SC bound undiluted |
| A. Human colostrum | | | |
| −1 | 42.00 | 21.96 | Too low to read |
| 0 | 50.24 | 20.32 | Too low to read |
| +1 | 27.43 | 11.70 | Too low to read |
| +2 | 15.04 | 9.20 | Too low to read |
| +1 | 11.98 | 9.20 | Too low to read |
| +2 | 10.80 | 8.16 | Too low to read |
| B. Human milk | | | |
| +3 | 6.98 | 5.49 | 6.13 |
| +3 | 2.50 | 3.04 | 2.65 |
| +3 | 1.64 | 1.50 | 1.44 |
| +3 | 1.42 | 1.77 | 1.51 |

It can be seen in the table that estimates of secretory IgA in colostrum using HM as a standard are low with both antisera. When "anti-SC free" is employed there are no antibodies to the bound determinant formed by the binding of the SC to IgA. With the antiserum to bound SC the antigenic determinants are in excess and little or no precipitate is formed, i.e. too low to read. On the other hand both antisera contain antibodies to determinants on free SC, which are also reactive when the SC is bound to IgA, so the estimates of secretory IgA in human milk via the SC free or SC bound are quite reasonable. Thus this process permits analysis of "specific" antisera for their content of antibodies to different antigenic determinants on the same sort of molecule, in this example, SC bound and free in human mammary secretions.

I claim:

1. Process for determining an immunologically-active material in a fluid, comprising using an inert gel matrix on a non-reactive support, said inert gel matrix containing an electrolyte and two opposite sides of said gel matrix being connected to an alternating current source means, applying an aliquot of a sample of the fluid onto said gel, covering the area of application with a solution containing an immunologically-specific counter-reactive material, applying an alternating current to said gel matrix, removing the unreacted soluble materials and observing the results of the immunological reaction at the area of application of the sample.

2. Process according to claim 1 wherein the immunologically active material is an antigen or an antibody and the counter-reactive material is an antibody specific for this antigen or antibody.

3. Process according to claim 1 wherein the immunologically active material is an antibody and the counter-reactive material a corresponding antigen.

4. Process according to claim 1 wherein the non-reactive support is a plate.

5. Process according to claim 1 wherein the results of the immunological reaction are observed after staining.

6. Process according to claim 1 wherein the non-reactive support is transparent.

7. Process according to claim 1 wherein the gel contains an additive decreasing the surface tension.

8. Process according to claim 1 wherein the immunologically active material is IgA.

9. Process according to claim 1 wherein the immunologically active material is IgG.

10. Process according to claim 1 wherein the immunologically active material is IgM.

11. Process according to claim 1 wherein the immunologically active material is C-Reactive Protein.

12. Process for determining the total protein content in a fluid by the method of claim 1, wherein the immunologically-active material is protein.

13. Process according to claim 1 wherein
(a) a gel matrix is formed on a plate of a nonreactive material
(b) a small volume of a biological fluid to be analyzed is applied onto the gel surface and it is allowed to be taken up by the gel,
(c) the area of application is covered with a solution containing a suitable concentration of an immunologically-specific counter-reactive material for the component to be determined in an amount greater than that of the first applied fluid so that during a sufficient period of time there is an excess of material enabling the components to react with each other to form an insoluble immunoprecipitate during the application of the alternating current,
(d) the gel matrix is washed at least once with a buffer solution and thereafter an absorption paper is pressed against the matrix so that the components which have not taken part in the reaction and remain still soluble are removed,
(e) the gel is rinsed and then pressed with an absorption paper again to a thin layer and the gel is dried with the last absorption paper in place,
(f) the paper is removed and the plate submerged in a solution of stain absorbable by the immunoprecipitate and the gel is destained so that the background of the stained areas becomes clear, and
(g) the stained areas are compared with a known color scale indicating the color intensity as a function of the amount of precipitate.

14. Process according to claim 13 wherein a fluid containing a number of different components to be determined is applied on the gel matrix, in a predetermined pattern in several areas; certain parts of that pattern are covered with solutions containing the desired specific counter-reactants, and the gel matrix is then treated according to steps d–g in claim 6.

15. The process of claim 13 further comprising the preparation of the color scale of step (g), wherein at least three different gradations of color are produced on the gel matrix by employing for said fluid to be analyzed at least three solutions, each containing a different predetermined amount of said component to be determined.

16. System suitable for determining immunologically-active material in a fluid comprising:
(a) an inert gel matrix containing an electrolyte on a non-reactive support;
(b) means for connecting said matrix with a source of alternating current; and
(c) an alternating current source means.

17. System according to claim 16 wherein the non-reactive support is a plate.

18. System according to claim 16 wherein the inert gel matrix contains an additive decreasing the surface tension.

19. System according to claim 16 wherein the plate is kept in a horizontal level position and the matrix connected by porous bridges to two vessels containing the electrolyte and in contact with the alternating current source via electrodes submerged in the vessels.

* * * * *